US005717732A

United States Patent [19]
Tam

[11] Patent Number: 5,717,732
[45] Date of Patent: Feb. 10, 1998

[54] CT IMAGING SYSTEM WITH INDEPENDENTLY MOVABLE MULTI-RESOLUTION DETECTOR

[75] Inventor: Kwok Cheong Tam, Edison, N.J.

[73] Assignee: General Electric Company, Schenectady, N.Y.

[21] Appl. No.: 553,800

[22] Filed: Oct. 23, 1995

[51] Int. Cl.⁶ .................................... G01N 23/00
[52] U.S. Cl. ..................... 378/4; 378/19; 378/22; 378/26
[58] Field of Search ..................... 378/4, 19, 22, 378/26

[56] References Cited

U.S. PATENT DOCUMENTS

| | | | |
|---|---|---|---|
| 4,442,534 | 4/1984 | Haendle et al. | 378/22 |
| 5,355,309 | 10/1994 | Eberhard et al. | 378/19 |

Primary Examiner—Craig E. Church
Attorney, Agent, or Firm—Marvin Snyder

[57] ABSTRACT

A system is provided for acquiring data for use in constructing a CT image of an object having a region of special interest, the system generally including an x-ray cone-beam source and an array detector having first and second zones, the resolution of the first zone being greater than the resolution of the second zone. Relative movement is established between the source and the object along a first path of translation, to position the source in a succession of view positions with respect to the object. The detector is moved along a second path of translation, which is substantially parallel to the first path, to position the detector at a succession of detector positions, each corresponding to one of the view positions. At each view position, the source is operated to project the beam toward the object, the beam axis being directed to intersect both the geometric center of the region of special interest, and the center point of the first resolution zone of the detector. The boundary of the first detector resolution zone is selected to substantially coincide with the boundary of the image of the special interest region when the detector is located at a detector position at which such image is of maximum dimensions.

12 Claims, 3 Drawing Sheets

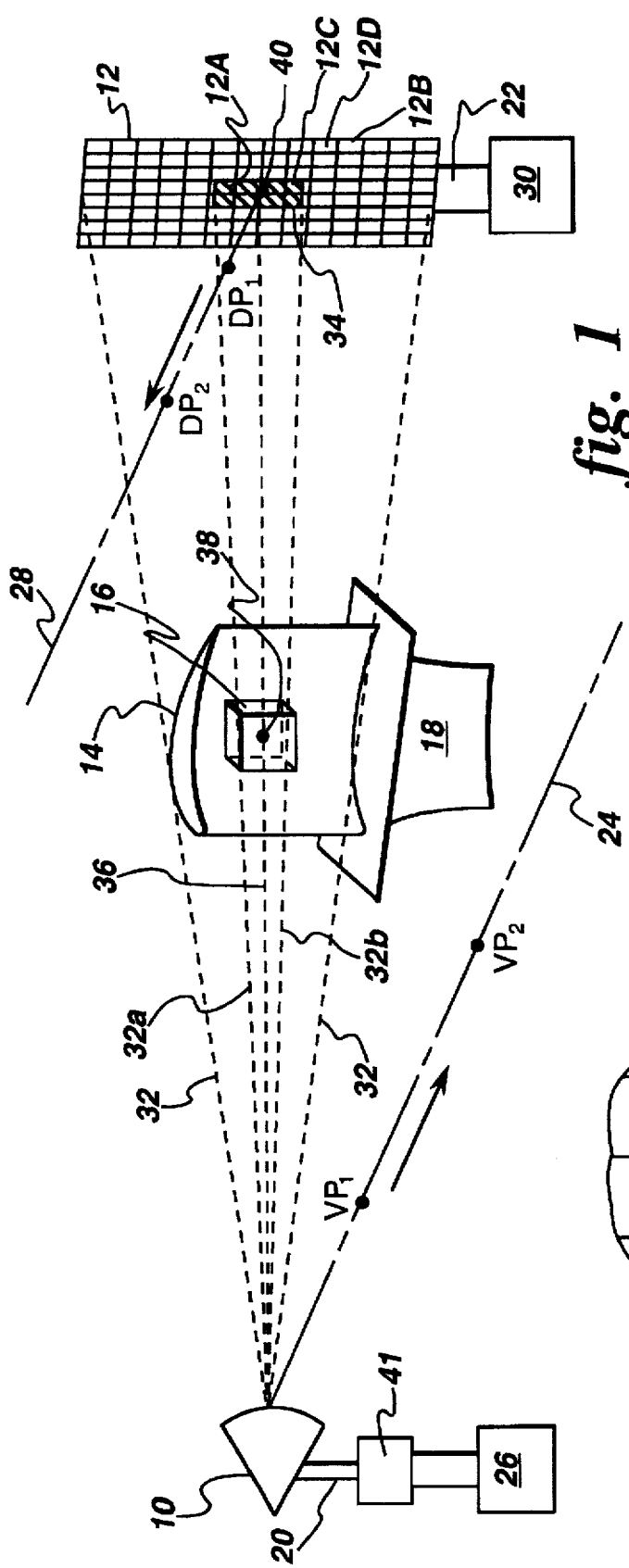
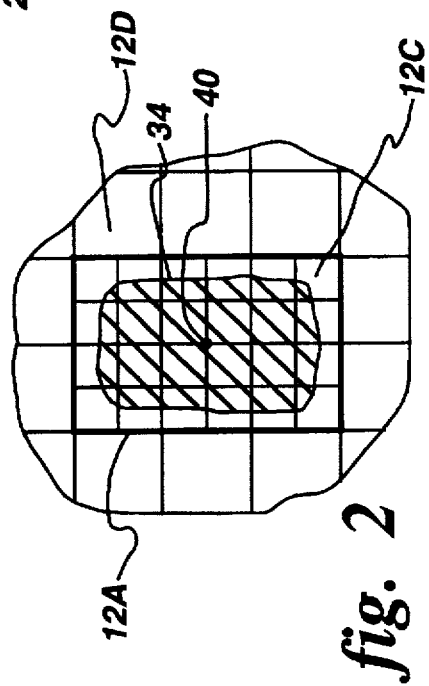

CT IMAGING SYSTEM WITH INDEPENDENTLY MOVABLE MULTI-RESOLUTION DETECTOR

BACKGROUND OF THE INVENTION

The invention disclosed and claimed herein generally pertains to a system for computed tomography (CT) imaging, wherein the x-ray source of the system is linearly moved or translated to scan an object of interest. More particularly, the invention pertains to a system of such type wherein the x-ray source is a cone beam source, the system x-ray detector has two or more regions of different resolution levels, and the detector is independently translatable with respect to the source.

One of the techniques currently used in constructing a CT image of an object, which is of particular importance in 3-dimensional (3D) CT imaging, makes use of a cone-beam x-ray source. In accordance with this technique, the cone-beam source irradiates the object with x-ray energy while traversing a scan path, to project an image of the object onto the plane of a detector, comprising an array of detection elements.

Previously, CT imaging arrangements were most commonly used for medical diagnostic purposes. In such applications, the source and detector are generally rotated with respect to a patient in performing a scan operation. However, there are also CT applications of growing importance in which a cone-beam source and associated detector are translated relative to an object to be imaged, rather than rotated therearound. For example, an imaging system of this type may be used in an industrial setting to inspect manufactured parts for defects.

In some applications of this latter type, a small region of the part may be of much greater interest than the remainder thereof. For example, the region of particular interest could include the portion of the manufactured part which is most critical for successful use thereof, which is most likely to contain small flaws or cracks, or which comprises an interior portion which cannot be viewed by a human inspector. Accordingly, such region of interest likely would need to be imaged with a comparatively high level of resolution. On the other hand, the remainder of the part or other object could be imaged with a lower level of resolution.

As is well known in the art, resolution in CT imaging is determined by detection element density of the CT detector array, i.e., the number of detection elements per unit of detector area. As is further well known, if the number of individual detector elements in a fixed detector area is substantially increased to provide a detector array of high resolution, the cost of detector manufacture likewise tends to be substantially increased. Moreover, each detector element provides a discrete data signal. Accordingly, a high resolution detector generates a substantially larger amount of acquired data. The number of data processing tasks which must be performed in order to construct an image is thereby correspondingly increased.

These concerns have led to the development of multi-resolution array detectors for CT imaging. In a multi-resolution detector, the detection elements are divided into different zones or regions. One of the zones has a high density of x-ray detection elements and is referred to as a fine resolution zone. Another region has a comparatively low density of detection elements, and is referred to as a coarse resolution zone. Detectors of this type are disclosed, for example, in commonly assigned U.S. Pat. No. 5,355,309, issued Oct. 11, 1994 to Jeffrey W. Eberhard and Kwok C. Tam, the inventor named herein.

It is readily apparent that a multi-resolution detector is very well suited for use in applications of the type referred to above, i.e., a CT system for imaging a part, wherein a small region of the part is of much greater interest than the remainder thereof. However, in using a multi-resolution detector, it is still advantageous to minimize the dimensions of the fine resolution zone thereof, for reasons stated above. In a CT system wherein relative linear motion occurs between the x-ray source and an object to be scanned, this may be achieved in accordance with the principles of the present invention.

SUMMARY OF THE INVENTION

The invention provides a system for acquiring data for use in constructing a CT image of an object having a region of special interest. In the invention, an x-ray source is disposed to project a beam of x-ray energy, the beam having an axis. An associated detector array is provided with first and second zones, the resolution of the first zone being greater than the resolution of the second zone, and the first zone having a center point. Relative movement is established between the source and the object along a first path of translation to position the source at a succession of view positions with respect to the object. The source is operated at each of the view positions to project the beam toward the object, so that the beam axis intersects the geometric center of the special interest region. The detector is moved along a second path of translation, which is substantially parallel to the first translation path, to position the detector at a succession of detector positions, each detector position corresponding to one of the view positions. For each detector position, the beam axis also intersects the center point of the first resolution zone of the detector. The detector is operated at respective detector positions to detect x-ray energy projected through the object from the source.

In one embodiment of the invention, the object remains stationary while the source is translated along the first path in a first direction to establish a succession of view positions, the detector being translated along the second path of translation in a direction opposite to the first direction. When the source is located at a given one of the view positions, it is separated by a first distance from the geometric center of the region of special interest, and is displaced along the first path from a first reference point by a first translational displacement. In like manner, when the detector is located at the detector position corresponding to the given view position, it is separated by a second distance from the geometric center, and is displaced along the second path from a second reference point by a second translational displacement. For each view position and corresponding detector position, the ratio of the first distance to the second distance is equal to the ratio of the first translational displacement to the second translational displacement.

In a second embodiment of the invention, the source is held stationary while the object is translated along the first path in a given direction, to establish the succession of view positions. The detector is translated to the succession of detector positions along the second path in the same direction as the direction of translation of the object.

An object of the invention is to provide a CT imaging arrangement including a multi-resolution CT detector having fine and coarse resolution zones, wherein the spatial dimensions of the fine resolution zone are minimized.

Another object is to provide an arrangement of such type, wherein an imaging operation is performed by establishing relative linear or translational movement between an x-ray source and the object to be imaged.

3

Another object is to provide an arrangement of such type wherein the detector is translated in a specified synchronous relationship with either translation of the source relative to a stationary object, or of the object relative to a stationary source.

These and other objects of the invention will become more readily apparent from the ensuing specification, taken together with the accompanying drawings.

BRIEF DESCRIPTION OF THE DRAWINGS

FIG. 1 is a view showing an object to be imaged in accordance with an embodiment of the invention.

FIG. 2 shows a portion of the detector for the embodiment of FIG. 1 in greater detail.

DETAILED DESCRIPTION OF THE PREFERRED EMBODIMENT

Figure 3:
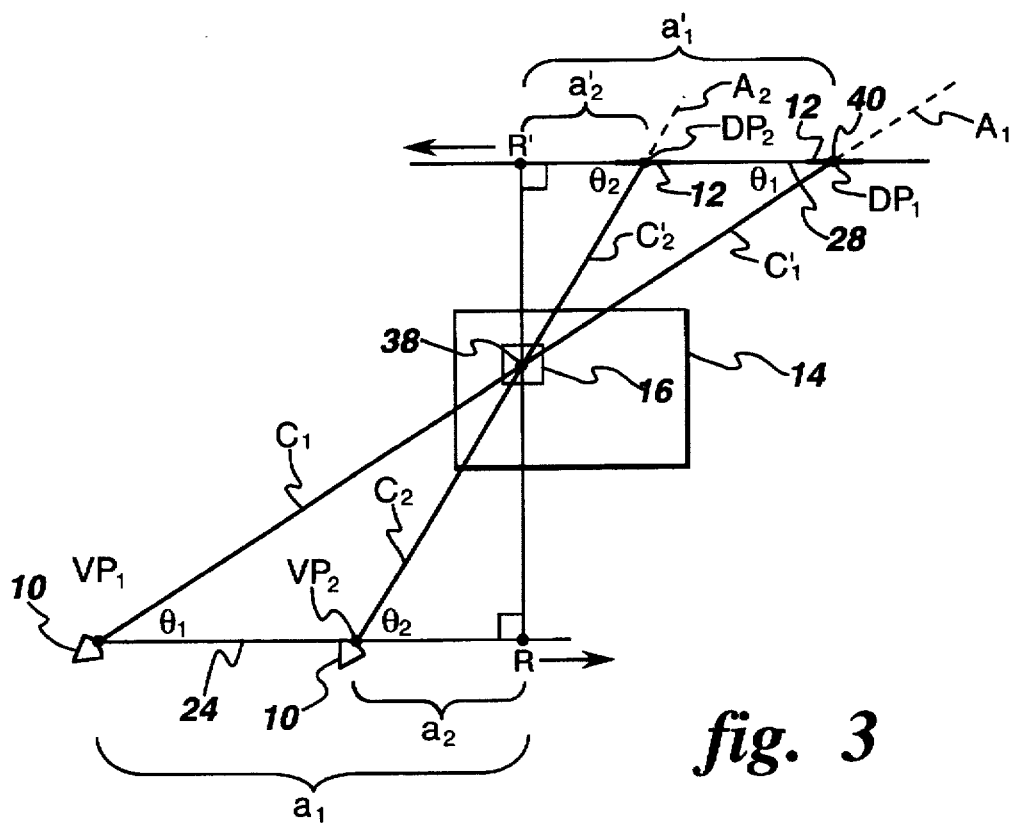
FIG. 3 is a geometric representation illustrating the invention with respect to the embodiment shown in FIG. 1.

Referring to FIG. 1, there is shown a cone-beam x-ray source 10 and an array detector 12, an object 14 being positioned therebetween. Cone-beam source 10 and detector 12 comprise known components of a conventional computed tomography (CT) cone-beam imaging system. Object 14 may be a part which has been machined or otherwise manufactured, and is to be imaged by the CT system, for example, to detect the presence of an internal flaw or defect, as stated above. It is to be understood that, consistent with the invention, object 14 could alternatively comprise a medical patient such as the subject of a medical diagnostic imaging operation, or other object.

Referring further to FIG. 1, there is shown a portion of object 14 comprising a region 16 which is of special or particular interest in the imaging process. For example, region 16 may comprise a portion of object 14 in which the presence of a crack or other defect would be particularly undesirable, or would be especially likely to occur. For an object 14 comprising a medical patient, region 16 could comprise body structure which needed to be imaged with particular clarity, in order to obtain a proper medical diagnosis.

Detector 12 comprises a matrix array of x-ray detection elements, each element generating a signal representing x-ray energy received thereby. Moreover, detector array 12 comprises a device known in the art as a multi-resolution detector array, i.e., an array having a zone 12A of comparatively high, or fine, resolution, and a zone 12B of lower or coarse resolution. Fine resolution zone 12A comprises a matrix array of x-ray detection elements 12C, which are much smaller than the x-ray detection elements 12D of coarse resolution zone 12B. Thus, the detection element density, i.e., the number of detection elements per unit area, is much greater for fine resolution zone 12A than for coarse resolution zone 12B. The general construction and operation of a multi-resolution detector suitable for use as array detector 12 is disclosed, for example, in U.S. Pat. No. 5,355,309, referred to above.

Referring further to FIG. 1, there is shown object 14 fixably mounted upon a stationary support structure 18, and cone-beam source 10 and detector 12 supported for translational movement by means of support structures 20 and 22, respectively. Each of the support structures 18, 20, and 22 is shown in generalized form, it being understood that the support structures respectively required for a specific application or implementation would readily occur to those of skill in the art. Source 10 and support structure 20 are translated along a linear scan path 24 by means of an actuating mechanism 26, likewise shown in generalized form, which could include a servo motor (not shown) or other known device. More specifically, source 10 is successively translated to a series of view positions $VP_i$, i=1, 2, . . . n. In like manner, detector 12 and support structure 22 are translated along a linear scan path 28 by means of a generalized actuating mechanism 30 to a succession of detector positions $DP_i$, i=1, 2 . . . n, where view and detector positions $VP_i$ and $DP_i$ respectively correspond to each other. By way of illustration, FIG. 1 shows view positions $VP_1$ and $VP_2$ along linear path 24, and further shows their respectively corresponding detector positions $DP_1$ and $DP_2$ on path 28. It is to be understood that a view position $VP_i$ is more specifically the $i^{th}$ location of the point source of cone-beam 32. Similarly, a detector position $DP_i$ is the ith location of the center point 40 of fine resolution zone 12A of detector 12.

Linear translation paths 24 and 28 are oriented to lie in parallel relation with each other. Moreover, source 10 and detector 12 are actuated to move in opposite directions along their respective paths, as shown by the arrows in FIG. 1. The respective movements of cone-beam source 10 and detector 12 are synchronized or coordinated, so that source 10 is located at a view position $VP_i$ coincident with the location of detector 12 at the detector position DPi. At each such location, source 10 projects a cone-beam 32 of x-ray energy toward object 14, some of the x-radiation passing therethrough and being detected by respective detection elements of detector 12. A portion of the energy traversing object 14, generally represented in FIG. 1 by rays 32a and 32b, passes through the region of interest 16 to project an image 34 thereof as, best viewed in FIG. 2, onto the detector 12.

At each corresponding pair of view and detector positions $VP_i$ and $DP_i$, cone-beam source 10 and detector 12 are respectively positioned so that the axis 36 of beam 32 is directed to intersect both the geometric center 38 of special interest region 16 of object 14, and also the center point 40 of fine resolution zone 12A of detector 12. Accordingly, the orientation of the image 34 of the special interest region, relative to center point 40 and fine resolution zone 12A, is substantially the same for each view-detector position pair. For the arrangement shown in FIG. 1, and for a given set of parameters therefor, the specific view and detector positions $VP_i$ and $DP_i$, at which the area of the image 34 is maximum, can be readily determined. The fine resolution zone 12A is then constructed so that the boundary thereof substantially coincides with the boundary of image 34 at its largest or maximum area. FIG. 1 shows a generalized actuating mechanism 41 mounted to selectively rotate source 10 at respective view positions $VP_i$, to direct axis 36 through geometric center 38 and center point 40 for each such position.

Referring further to FIG. 2, there is shown image 34 of region of interest 16 projected onto zone 12A of detector 12, for the view-detector position pair for which image 34 is of such maximum area. For the above condition that beam axis 36 intersects both geometric center 38 and center point 40 for each view position $VP_i$, the boundary of image 34 will not extend beyond zone 12A for any other view-detector position pair. The dimensions of fine resolution zone 12A are thereby minimized, since it is not necessary to provide an additional margin for zone 12A, in anticipation that such extension might occur.

In accordance with the invention, a comparatively simple technique has been developed to determine the detector position $DP_i$ relative to the corresponding view position $VP_i$, in order to ensure that source 10 and detector 12 will respectively be positioned to enable the above condition pertaining to beam axis intersection to be met for all values of i. Referring to FIG. 3, there are shown view positions $VP_1$ and $VP_2$ on cone-beam linear translation path 24, and their respectively corresponding detector positions $DP_1$ and $DP_2$ on detector translation path 28. There is further shown a line RR' in orthogonal relationship with both linear paths 24 and 28, which are respectively intersected by the line RR' at reference points R and R'. The line RR' also intersects the geometric center 38 of special interest region 16 of object 14. View position $VP_1$ is located a distance a1 from the reference position R along translation path 24, and view position $VP_2$ is located at a distance $a_2$ therefrom. Thus, $a_1$ and $a_2$ are the respective translational displacements of $VP_1$ and $VP_2$. Similarly, detector position $DP_1$ is located at a distance a11 from reference position R' along translational path 28, and detector position $DP_2$ is located at a distance $a_2'$ from R'. $a'_1$ and $a'_2$ are thus the respective translational displacements of $DP_1$ and $DP_2$.

Referring further to FIG. 3, there is shown axis 36 of the cone-beam of source 10 lying along a line $A_1$ when directed from view position $VP_1$ through geometric center 38, and through center point 40 at detector position $DP_1$. In like manner, the cone-beam axis lies along a line $A_2$ when directed from view position $VP_2$ through geometric center 38 and through center point 40 at detector position $DP_2$. Since linear paths 24 and 28 are parallel, the axis $A_1$ intersects both paths at an angle $\theta_1$, and axis $A_2$ intersects both paths at an angle $\theta_2$.

In FIG. 3, $c_1$ is shown as the distance between view position $VP_1$ and geometric center 38 of object 14, and $c_1'$ is shown as the distance between geometric center 38 and the corresponding detector position $DP_1$. Since $\cos\theta_1$ equals $a_1/c_1$, and since $\cos\theta_1$ also equals $a_1'/c_1'$, $a_1/c_1 = a'_1/c'_1$. It follows that $\alpha_1/\alpha'_1 = c_1/c'_1$. Thus, to ensure that the above condition pertaining to beam axis intersection is met for $VP_1$ and $DP_1$, their respective translational displacements $a_1$ and $a'_1$ are selected so that the ratio thereof is equal to the ratio of $c_1$ to $c_1'$.

In FIG. 3, $c_2$ and $c_2'$ are the respective distances between $VP_2$ and geometric center 38, and between $DP_2$ and geometric center 38. Accordingly, $\cos\theta_2 = a_2/c_2 = a'_2/c'_2$, so that $a_2/c_2 = a'_2 = a'_2/c_2$. Thus, the translational displacements of $VP_2$ and $DP_2$ are likewise selected so that the ratio thereof is equal to the ratio between the distance from $VP_2$ to geometric center 38, and the distance $DP_2$ to geometric center 38.

Figure 4:
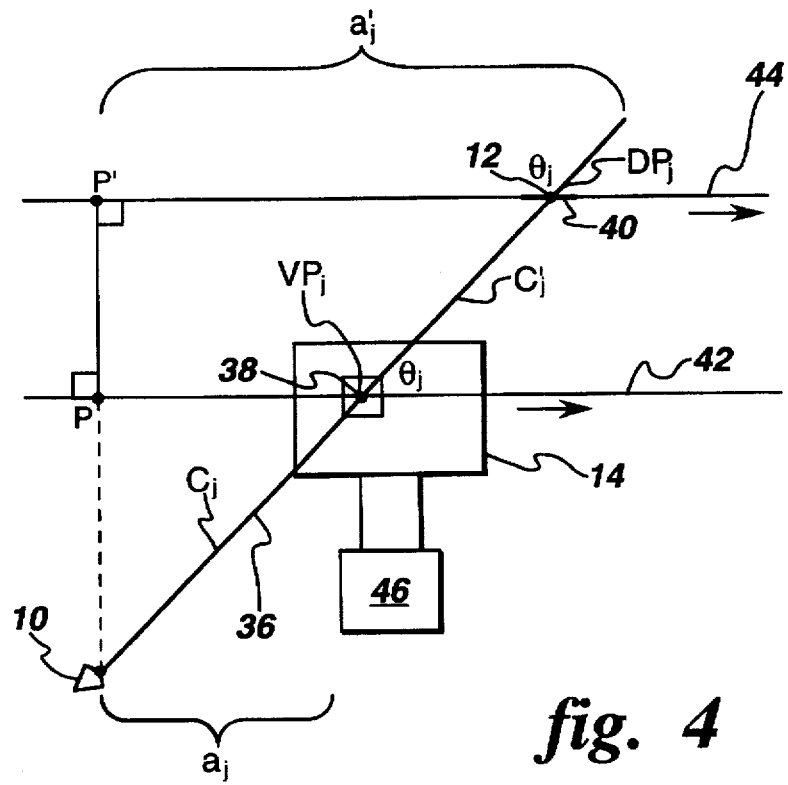
FIG. 4 is a geometric representation illustrating a modification of the embodiment shown in FIG. 1.

Referring to FIG. 4, there is shown a modification of the invention wherein cone-beam source 10 is constrained against translational movement, although the beam projected thereby can be rotated through an arc, such as by an actuating mechanism 41 (not shown in FIG. 4). To establish a succession of view positions $VP_j$, j=1, 2, . . . n, object 14 is translated relative to source 10 along a linear path 42, the direction of movement of object 14 being rightward as viewed in FIG. 4. When object 14 is moved to a position $VP_j$, detector 12 is also translated rightwardly, as viewed in FIG. 4, along a linear path 44 to a corresponding detector position $DP_j$, the linear paths 42 and 44 being in parallel relationship with each other. Also, when object 14 and detector 12 are respectively located at corresponding positions $VP_j$ and $DP_j$, source 10 is oriented to project a cone-beam 32 so that axis 36 thereof intersects both geometric center 38 of the region of special interest 16 of object 14, and also intersects the center 40 of the fine resolution zone 12A of detector 12. Axis 36 intersects both linear paths 42 and 44 at an angle $\theta_j$. Object 14 is actuated to move along path 42, for example, by means of a generalized actuating mechanism 46. It is to be understood that a view position $VP_j$ is more specifically the $j^{th}$ location along path 42 of geometric center 38 of object 14. Similarly, a detector position $DP_j$ is the $j^{th}$ location along path 44 of the center point 40 of fine resolution zone 12A of detector 12.

FIG. 4 further shows a line $PP_i$ in orthogonal relationship with each of the linear paths 42 and 44, and respectively intersecting such paths at the reference points P and P'. Line PP' also intersects cone-beam source 10. FIG. 4 shows the translational displacement of the view position $VP_j$ along linear path 42, from reference point P, to be $a_j$, and shows the translational displacement of $DP_j$ along path 44, from the reference point P', to be $a_j'$. The distance between $VP_j$ and the point source of source 10 is shown to be $c_j$, and the distance between $DP_j$ and the point source is shown to be $c'_j$. Thus, to ensure that beam axis 36 intersects both geometric center 38 and center point 40 of detector 12 for each view position $VP_j$ and detector position $DP_j$, in order to minimize the required dimensions for fine resolution zone 12A as described above, respective parameters $a_j$, $a_j'$, $c_j$ and $c_j'$ are selected so that $a_j/a_j' = c_j/c_j'$.

Figure 5:
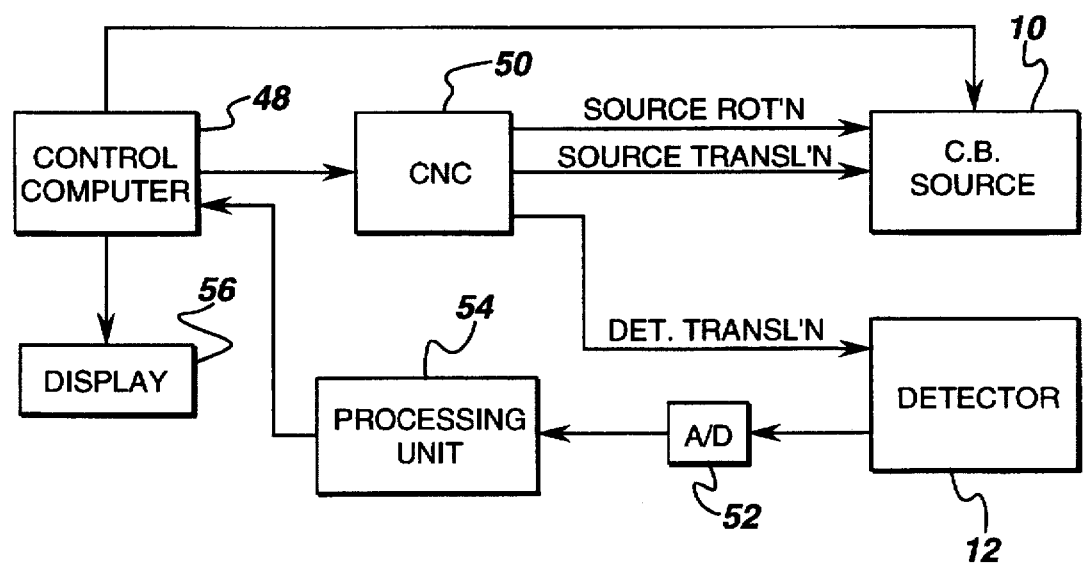
FIG. 5 is a block diagram showing a control arrangement for use in connection with the embodiment of FIG. 1.

Referring to FIG. 5, there is shown a control computer 48, such as the workstation computer of a conventional CT imaging system, coupled to operate a computer numerical control (CNC) 50. Control 50 is a control device of a type well known in the robotics, machine tool and other arts for controlling complex mechanical motion with respect to three or more axes. More particularly, control 50 generates control signals to simultaneously control translation of one or more mechanical structures along a number of different axes, and/or rotation thereof about one or more different axes. Thus, Control 50 couples control signals to translate source 10 not shown in FIG. 5 along linear path or axis 24 to successive view positions $VP_i$, as described above. Signals, for example, may be coupled to actuate mechanism 26. Similarly, Control 50 couples signals to actuating mechanism 30, to successively move detector 12 along linear path or axis 28 to corresponding detector positions $DP_i$. Control 50 further couples a rotation signal to a device such as mechanism 41 shown in FIG. 1 to selectively rotate source 10 at respective view positions $VP_i$ to direct the cone-beam axis 36 through geometric center 38 and center point 40, as described above. Operation of source 10 is controlled by a signal coupled thereto from control computer 48.

Referring further to FIG. 5, there is shown the output of detector 12, comprising a set of data signals in analog form representing the radiation levels detected by respective detection elements 12C and 12D, coupled to analog-to-digital converter 52. Converter 52 converts the data signals into digital form, and couples them to processing unit 54. Unit 54 places the data in condition for use by computer 48 to generate an image of the object 14, such as by means of display 56.

Figure 6:
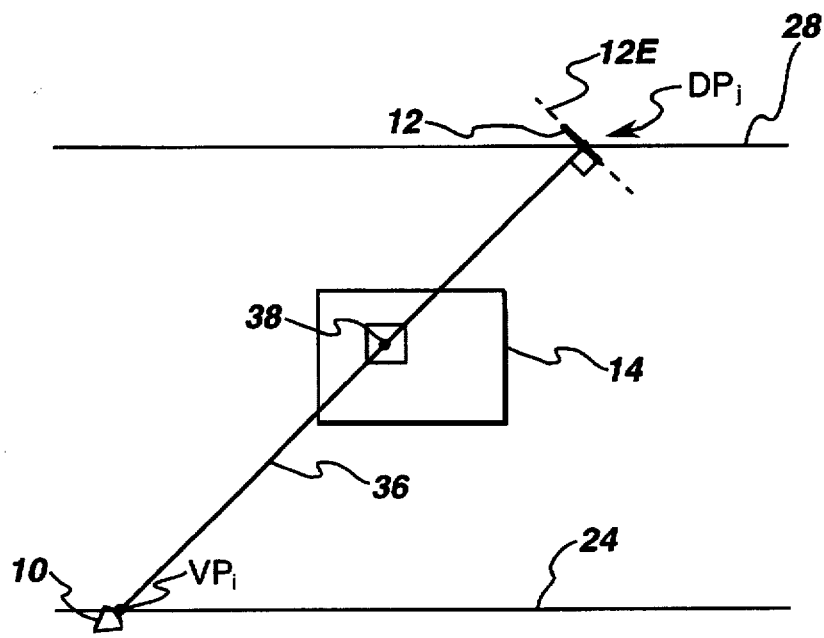
FIG. 6 is a view showing another modification of the invention.

Referring to FIG. 6, there is shown a modification of the invention, wherein the detector 12, when located at a detector position $DP_i$ corresponding to a view position $VP_i$, is rotated so that the detector face lies in a plane 12E. Plane 12E is in orthogonal relationship with the beam axis 36 projected from the source 10 at the corresponding view position VPi. It has been found that such rotation of the detector 12 allows the dimensions of fine resolution zone 12A to be further reduced, for a given set of parameters for the embodiment of the invention as shown in FIG. 1. The detector 12 may be rotated by an actuating mechanism (not shown) which receives a detector rotation signal from Control 50.

In the embodiment of the invention shown in FIG. 4, detector 12 may also be rotated into orthogonal relationship with cone-beam axis 36 at respective detector positions $DP_j$.

Obviously many other modifications and variations of the present invention are possible in light of the above teachings. It is therefore to be understood that within the scope of the disclosed concept, the invention may be practiced otherwise than as specifically described.

What is claimed is:

1. A method for acquiring data for use in constructing a CT image of an object having a region of special interest, said method comprising:

providing an x-ray source disposed to project a beam of x-ray energy, said beam having an axis;

providing an array detector having first and second zones, the resolution of said first zone being greater than the resolution of said second zone, said first zone having a center point;

establishing relative movement between said source and said object along a first path of translation to position said source in a succession of view positions with respect to said object;

at each of said view positions, operating said source to project said beam toward said object, and to direct said beam axis to intersect the geometric center of said region of special interest;

moving said detector along a second path of translation which is substantially parallel to said first path to position said detector at a succession of detector positions, each corresponding to one of said view positions, said beam axis intersecting said center point of said first zone at each of said detector positions; and operating said detector at each of said detector positions to detect x-ray energy projected through said object from said source.

2. The method of claim 1, wherein:

said object is kept stationary as said source is translated along said first path in a first direction to said succession of view positions; and said detector is translated to said succession of detector positions along a second path in a direction opposite to said first direction.

3. The method of claim 2, wherein:

a given one of said view positions is separated by a first distance from said geometric center, and is spaced along said first path from a first reference point by a first translational displacement;

the detector position corresponding to said given view position is separated by a second distance from said geometric center, and is spaced along said second path from a second reference point by a second translational displacement; and for said given view position the ratio of said first distance to said second distance is equal to the ratio of said first translational displacement to said second translational displacement.

4. The method of claim 1, wherein:

said source is kept stationary as said object is translated along said first path in a specified direction; and said detector is translated to said succession of detector positions along a second path in the same direction as said object is translated.

5. The method of claim 4, wherein:

when said object has been translated to establish a given one of said view positions, the geometric center of said object is separated by a first distance from said source, and is spaced along said first path from a first reference point by a first translational displacement;

the detector position corresponding to said given view position is separated by a second distance from said source, and is spaced along said second path from a second reference point by a second translational displacement; and for said given view position the ratio of said first distance to said second distance is equal to the ratio of said first translational displacement to said second translational displacement.

6. The method of claim 1 wherein said detector has a detector face lying within a plane, and said method includes the step of:

selectively orienting said detector with respect to said beam axis so that when said detector is located at a given detector position, said plane and said beam axis are in substantially orthogonal relationship.

7. The method of claim 1 wherein:

at each of said detector positions an image of said region of special interest is projected onto said first zone of said detector, one of said projected images of said region having an area which is larger than the other projected images thereof; and the boundaries of said first detector zone are selected to substantially coincide with the boundaries of said projected image having said larger area.

8. Apparatus for acquiring data for use in constructing a CT image of an object having a region of special interest, said apparatus comprising:

an x-ray source disposed to project a beam of x-ray energy, said beam having an axis;

an array detector having first and second zones, the resolution of said first zone being greater than the resolution of said second zone, said first zone having a center point;

means for establishing relative movement between said source and said object along a first path of translation to position said source in a succession of view positions with respect to said object, said beam axis being directed to intersect said geometric center of said region of special interest for each of said view positions;

means for moving said detector along a second path of translation substantially parallel to said first path to position said detector at a succession of detector positions, each corresponding to one of said view positions;

means for selectively moving said source with respect to said object and said detector to direct said beam axis to intersect said geometric center of said region of special interest and said center point of said first zone for each of said view positions; and means for processing signals received from said detector to provide said data, said signals representing x-ray energy projected through said object from said source and detected by said detector at said detector positions.

9. The apparatus of claim 8 wherein said apparatus includes:

first means for moving said source along said first path in a first direction while said object remains stationary; and second means for moving said detector along said second path in a direction opposite to said first direction.

10. The apparatus of claim 9 wherein:

a given one of said view positions is separated by a first distance from said geometric center, and is spaced along said first path from a first reference point by a first translational displacement;

the detector position corresponding to said given view position is separated by a second distance from said geometric center, and is spaced along said second path from a second reference point by a second translational displacement; and for said given view position the ratio of said first distance to said second distance is equal to the ratio of said first translational displacement to said second translational displacement.

11. The apparatus of claim 8 wherein said apparatus includes:

first means for translating said object along said first path in a first direction to successively establish said view positions while said source remains stationary; and second means for translating said detector along said second path in the same direction as said first direction.

12. The apparatus of claim 11 wherein:

when said object has been translated to establish a given one of said view positions, the geometric center of said object is separated by a first distance from said source, and is spaced along said first path from a first reference point by a first translational displacement;

the detector position corresponding to said given view position is separated by a second distance from said source, and is spaced along said second path from a second reference point by a second translational displacement; and for said given view position the ratio of said first distance to said second distance is equal to the ratio of said first translational displacement to said second translational displacement.

* * * * *